United States Patent
Rutschmann

(10) Patent No.: US 7,433,502 B2
(45) Date of Patent: Oct. 7, 2008

(54) THREE-DIMENSIONAL, DIGITIZED CAPTURING OF THE SHAPE BODIES AND BODY PARTS USING MECHANICALLY POSITIONED IMAGING SENSORS

(75) Inventor: Dirk Rutschmann, Stuttgart (DE)

(73) Assignee: corpus.e AG, Stuttgart (DE)

( * ) Notice: Subject to any disclaimer, the term of this patent is extended or adjusted under 35 U.S.C. 154(b) by 323 days.

(21) Appl. No.: 10/546,704

(22) PCT Filed: Mar. 3, 2004

(86) PCT No.: PCT/EP2004/002136

§ 371 (c)(1),
(2), (4) Date: Aug. 22, 2005

(87) PCT Pub. No.: WO2004/078040

PCT Pub. Date: Sep. 16, 2004

(65) Prior Publication Data

US 2006/0140463 A1      Jun. 29, 2006

(30) Foreign Application Priority Data

Mar. 5, 2003    (DE) ................................ 103 09 788

(51) Int. Cl.
*G06K 9/00* (2006.01)
(52) U.S. Cl. ........................................ 382/128; 382/154
(58) Field of Classification Search ................. 382/128, 382/154
See application file for complete search history.

(56) References Cited

U.S. PATENT DOCUMENTS

| 706,459 | A | | 8/1902 | Selke | |
|---|---|---|---|---|---|
| 3,690,242 | A | | 9/1972 | Cruickshank | |
| 5,911,126 | A | * | 6/1999 | Massen | ..................... 702/153 |
| 6,463,351 | B1 | * | 10/2002 | Clynch | ......................... 700/163 |
| 6,546,356 | B1 | * | 4/2003 | Genest | ........................ 702/153 |
| 6,829,377 | B2 | * | 12/2004 | Milioto | ........................ 382/128 |
| 7,095,886 | B2 | * | 8/2006 | Massen | ........................ 382/154 |
| 2001/0014171 | A1 | * | 8/2001 | Iijima et al. | .................. 382/154 |
| 2002/0038263 | A1 | * | 3/2002 | Massen | ........................ 705/27 |
| 2003/0042401 | A1 | * | 3/2003 | Gartner et al. | ............ 250/208.1 |

(Continued)

FOREIGN PATENT DOCUMENTS

EP        0 760 622 B1    11/1995

(Continued)

*Primary Examiner*—Samir A. Ahmed
*Assistant Examiner*—Michael Vanchy, Jr.
(74) *Attorney, Agent, or Firm*—Stuart J. Friedman

(57) ABSTRACT

There is described a photogrammetric method and an arrangement for the three-dimensional digitizing of bodies and body parts (26) which are covered with a marked, elastic cover (14), which comprises high-contrast marks which are photogrammetrically analysable, and which are photographed from different shooting positions. For the purpose, at least one camera (22) is moved around the body with a simple, inaccurate guide and images overlapping each other are taken from different positions in space to cover both the body and several of the marks (10) of the support (12). Methods of photogrammetry as well as digital image processing and pattern recognition provide precise space coordinates of the body to be digitized. One exemplary application is the digitizing of the foot/lower leg portion for the selection or custom manufacture of anatomically well-fitting footwear, the digitizing of the leg portion for the manufacture or selection of well-fitting compression stockings.

23 Claims, 2 Drawing Sheets

U.S. PATENT DOCUMENTS

Figure 1:
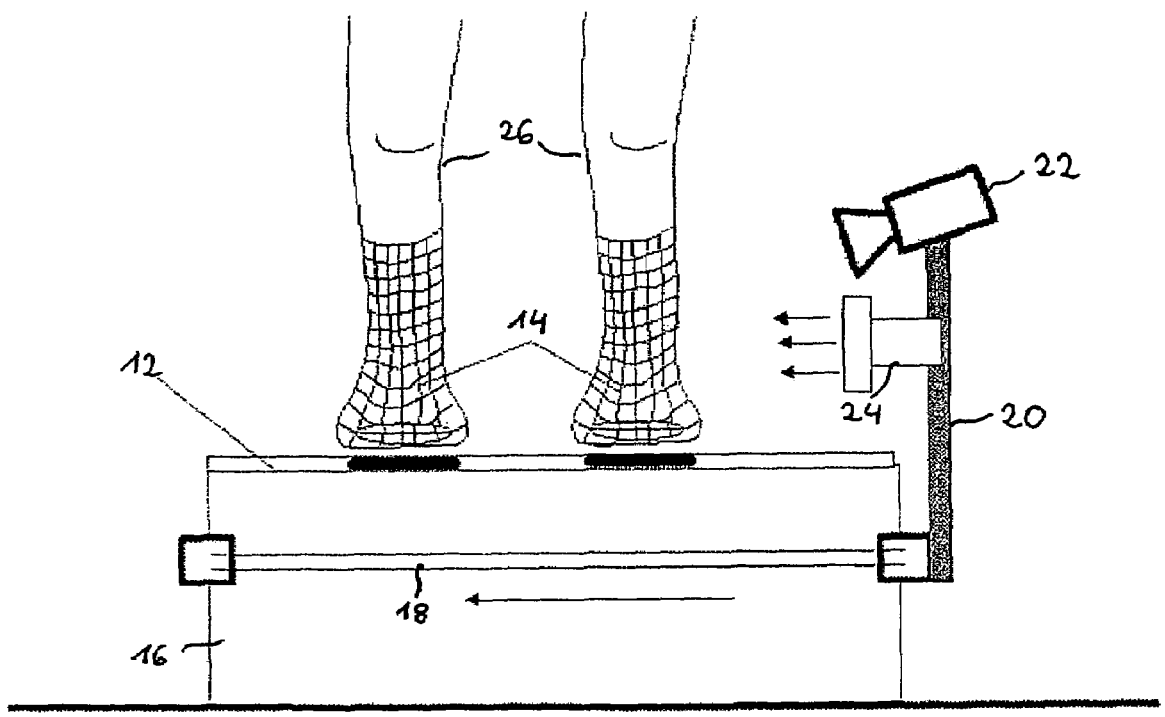

2003/0137510 A1* 7/2003 Massen ............... 345/420
2003/0142863 A1* 7/2003 Massen ............... 382/154
2004/0032595 A1* 2/2004 Massen ............... 356/603
2005/0031193 A1* 2/2005 Rutschmann et al. ....... 382/154

FOREIGN PATENT DOCUMENTS

EP          0 958 782  A1    11/1999

* cited by examiner

THREE-DIMENSIONAL, DIGITIZED CAPTURING OF THE SHAPE BODIES AND BODY PARTS USING MECHANICALLY POSITIONED IMAGING SENSORS

The sensing of the spatial shape, i.e. of the three-dimensional coordinates of the surface of bodies and body parts like, for example, the human torso, the leg portions, the feet etc. for the selection of well-fitting clothes, orthopaedic or sports equipment or for the dimensionally accurate manufacture of these products, for the acquisition of anatomically and medically interesting data is nowadays carried out with relatively costly optical 3D scanners which usually operate on the basis of laser triangulation, strip projection or near range photogrammetry. An especially economical arrangement of such a scanner is the so-called "MagicalSkin Scanner" from the firm of corpus.e AG, Stuttgart (www.corpus-e.com). Here the body part to be digitized is covered with a specially marked elastic, tight-fitting cover and photographed using a common digital camera, without support and from several views overlapping each other. The photogrammetric recording, i.e. the allocation of corresponding marks from the individual images is carried out with the special codification of these marks as well as an equally marked bottom plate on which the client to be digitized stands. This method is described in a series of granted patents and patent applications such as for instance in generic patent EP 0 760 622: Digital sensing process and arrangement for the 3-dimensional shape in space of bodies and body parts (inventor: Robert Massen).

The freehand positioning of the digital camera around the client standing erect results in an extremely economical solution since no mechanical set-ups, tripods or calibrated arrangements for lighting and cameras are required. However, this requires a certain practice in handling the camera so that the individual image shots sufficiently overlap each other and the image fields cover the body part to be photographed rather completely. This practice does not always exist, more particularly in shops where staff are steadily changing. The wrong handling of the camera may result in wrong shots, i.e. ones that cannot be evaluated correctly. Therefore both a technical and an economical advantage would be reached if the camera could be moved to the various shooting positions, which are defined only approximately in space, independently of the operator personnel's skill while maintaining the advantages of this extremely economical digitizing principle.

In the above-cited patent, an arrangement of several cameras fixedly positioned in space for taking photos of the body part is described, inter alia, the contemporaneous shooting and, accordingly, the short scanning time being mentioned as an advantage. However, this advantage comes with increased costs due to the numerous cameras needed, their mountings, the connections to the evaluating computer etc.

It is also known, in optical strip projection systems or systems which cover the silhouette of the human body under several views, to put the body to be digitized onto a turntable and rotate it, motor-driven, into the different shooting positions. This approach is costly, too, since this mechanism must bear the whole weight. Also, it is unpleasant for older clients, in particular, since they must stand upright and immovable without being able to hold on to something during the motor-driven rotation.

Therefore it is technically and economically interesting to dispose of an economical digitizing system of the Magical-Skin type, wherein the individual photos, which overlap each other, may even safely be taken by staff out of practice, wherein the client's whole body need not be moved into the individual shooting positions and wherein the costs of the whole system remain low.

In accordance with the invention, this is achieved by a method wherein the body, the body part or the body parts to be digitized is or are covered with an elastic, tight-fitting cover which comprises high-contrast marks that are photogrammetrically analysable. The body, the body part or the body parts is or are put onto a support which is also provided with photogrammetric marks. At least one imaging sensor is mechanically moved around the body, the body part or the body parts on an approximately circular path in space and at least one image is respectively taken in successive shooting positions, whose image cutouts partially overlap each other, and which covers both the body, the body part or the body parts and, simultaneously, several of the marks of the support. These images are evaluated by methods of photogrammetry and digital image processing and pattern recognition, such that precise space coordinates of the photographed body, the body part or the body parts are determined.

When using this method, the patient need not be moved. The camera is guided on an about circular path, predetermined shooting positions are reached mechanically, independently of the operator personnel, so that overlapping images are always ensured which enable subsequent evaluation of the photographed photogrammetric marks. The sensor guide may be configured in a simple manner since the precise position of the camera or, respectively, of the imaging sensor need not be known in the method according to the invention. If there is sufficient overlapping, the precise space coordinates of the body or the body parts may be determined without knowledge about the exact space position of the camera via known photogrammetric methods on the basis of the marks on the support and on the body to be digitized. The mechanical positioning in predetermined shooting positions ensures this sufficient overlapping.

With this embodiment, different bodies or body parts may be taken into account even more flexibly, for instance a denser image sequence is automatically evaluated when a body hides an above-average number of marks fixed on the support.

In a further embodiment, the image sensor may be adjusted in the vertical and/or azimuthal direction in addition to the mechanical movement around the body, the body part or the body parts. This embodiment also allows a more flexible adaptation to different body shapes, for instance two image series in different heights would be conceivable for images of the whole lower part of a human body.

The invention also relates to an arrangement for the three-dimensional, digitized sensing of spatial shape of bodies or body parts. This one includes a support which is provided with high-contrast marks which are photogrammetrically analysable and serves as a floor area for the body, the body part or the body parts to be digitized which is or, respectively, are covered with an elastic, tight-fitting cover. This cover also comprises marks which are photogrammetrically analysable. Furthermore, the arrangement includes at least one imaging sensor and at least one approximately vertical holder, to which the imaging sensor is attached, as well as a base, on which the support rests and which carries along its periphery an approximately circular mechanical guide along which the holder is guided. Moreover, the arrangement includes means for moving the holder together with the imaging sensor to successive shooting positions whose image cutouts overlap each other and simultaneously cover the body, the body part or the body parts to be digitized and several of the support marks which are photogrammetrically analysable, as well as means for triggering image shots in the shooting positions.

Besides, the arrangement includes a computer to which the images taken are transmitted and which calculates by methods of image processing, pattern recognition and photogrammetry, the spatial shape of the body, the body part or the body parts.

A further inventive idea resides in configuring the camera mounting to be tiltable so that the projecting arm or holder may be tilted towards the marked support.

A further inventive idea resides in moving the imaging sensor on an elliptic track around the body parts to be digitized. Especially when an image of the foot/leg portion of a standing person is taken, this has the advantage that the distances between the camera and the leg/foot are approximately constant.

The rotary motion of the camera holder may be effected by an electric drive, but also by a mechanical drive. Since the weight of the imaging sensor and the lighting is especially low, no high forces are needed therefor.

A further inventive idea resides in simultaneously guiding several cameras on the circular path in order to reduce the number of shooting positions and, accordingly, the shooting time.

A further inventive idea resides in that several cameras are mounted on the camera holder so that each one covers a different image field with the same or with differing image field sizes.

A further inventive idea resides in that for the optical sensing of a vertical range, which is larger than the one to be sensed from one camera position, the camera photographs the foot/leg portion circularly around the client in different heights, relative to the bottom plate. For the purpose, the camera mounting is provided with an additional vertical linear guide and the camera is positioned in different vertical positions. According to the invention, the camera may alternatively be brought into different angular positions.

All these variants in accordance with the invention have in common that they may be realised with little technical expenditure since, as has already been mentioned above, it is not required to know the precise position in space of the imaging sensor.

A further inventive idea resides in that the camera is a video camera which continuously takes images during the mechanical movement around the body and that automatically by evaluating the bottom plate marks, using methods of pattern recognition, those individual images, which partially overlap each other, are determined which are required for the photogrammetric evaluation. Indeed, the person skilled in image processing and pattern recognition is familiar with extracting the bottom mark range from the respective individual images of the video sequence, decoding these marks and determining therefrom the angular position of the shot concerned. The photogrammetric evaluation typically needs 10 shots around the body, i.e. one shot every 36 degrees. By comparing the shooting positions, which are determined with the aid of pattern recognition, with this shooting rule, all those images of the video sequence may be deleted which are not needed for the photogrammetric evaluation. Creating video shots is advantageous in comparison to the single image shot insofar as the image release need only be actuated once, the mechanical movement does not need to be stopped in the individual shooting positions and thus may be effected quicker on the whole.

A further inventive idea resides in that several image sensors, which are disposed vertically on top of each other, are moved around the body in order to sense larger bodies like, for instance, the whole person standing upright, too.

A further inventive idea resides in that an image sensor is repeatedly moved around the body in different heights, relative to the marked support, in order to sense larger bodies like, for instance, the whole person standing upright, too.

A further inventive idea resides in that, within the plate on which the client stands, sensors for sensing physical quantities like foot pressure measuring fields, weight measuring fields, sensors for the electroimpedance-technical determination of the body fat content and similar sensors are mounted, which are known to the expert in orthopaedics and medicine. Thus, important anatomical and physiological data of the patient may be sensed, simultaneously with the digitizing of the leg/foot portion, which data must also be taken into account for the selection or, respectively, the custom manufacture of some footwear.

A further inventive idea resides in that, after photographing the body covered with the elastic cover, the undressed body is photographed in approximately the same position and anatomically and medically interesting images are taken.

A further inventive idea resides in that these images of the undressed body are superimposed on the photogrammetrically established 3D data set in the form of a texture.

The described use of the foot/leg digitizing has to be understood in an exemplary manner. The inventive idea also covers the digitizing of other body parts like the torso, for instance. It is easy for the person skilled in the art to configure the mechanical arrangement of the camera and the guides and drives required for moving it correspondingly.

The inventive idea is not at all restricted just to the digitizing of human or biological bodies, but includes all objects which are covered with a tight-fitting marked cover for digitizing.

Figure 2:
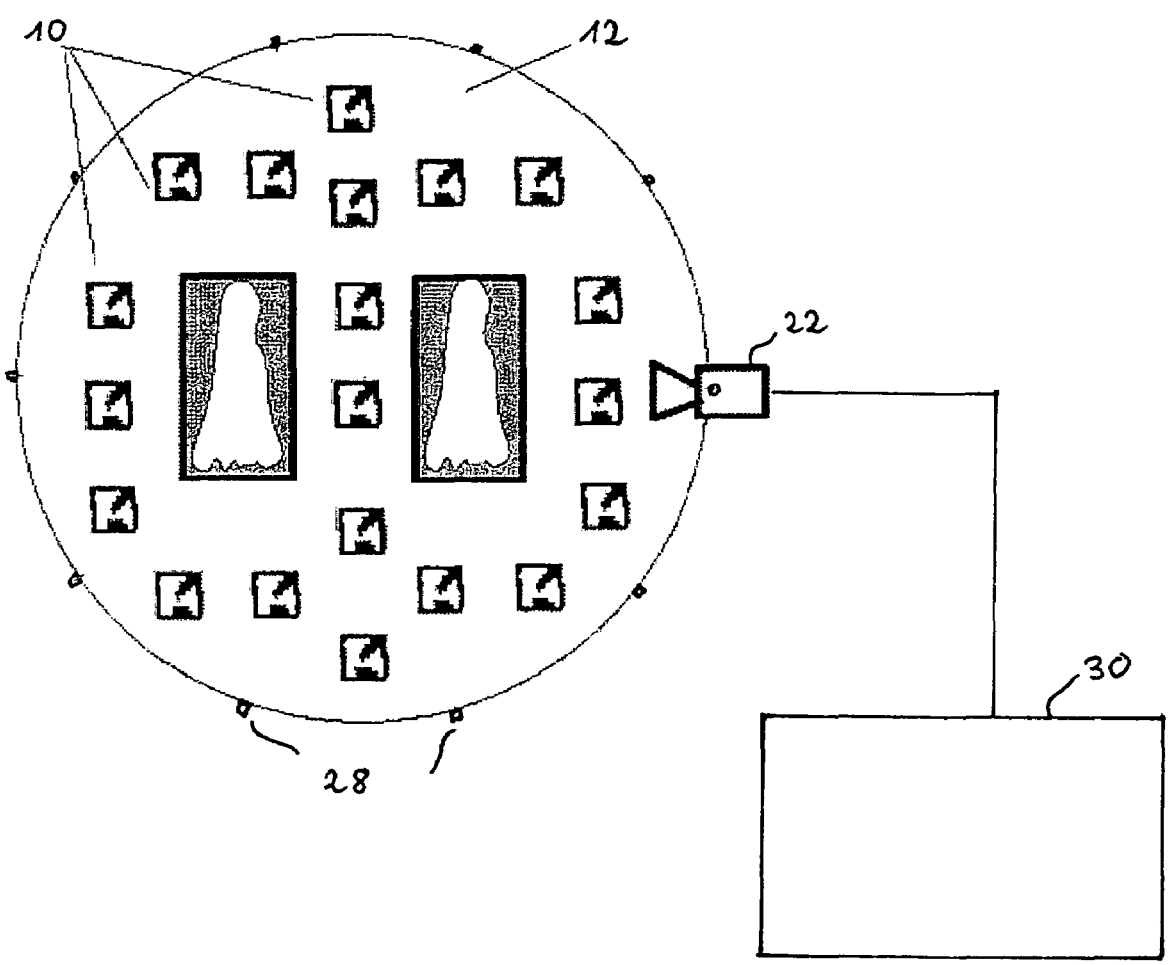

Further advantages and features of the invention result from the subclaims and the following description of an embodiment, namely an arrangement and a method for the 3D digitizing of the clients' feet within the framework of the sale of well-fitting footwear upon reference to the drawing; therein FIG. 1 is a schematic front view of an arrangement for the three-dimensional, digitized sensing of lower legs according to the invention; and FIG. 2 is a schematized plan view on a support of the arrangement according to the invention.

As is shown in the front view of FIG. 1, a client stands upright on a support 12 provided with marks 10 which are photogrammetrically analysable and wears two elastic, tight-fitting stockings 14 which are provided with high-contrast marks which are equally photogrammetrically analysable. Support 12 is situated on a flat, circular base 16 along the periphery of which a circumferential guide 18 extends. In this guide 18, a vertical holder 20 is moved which carries an imaging sensor 22 and a lighting device 24. This holder 20 is moved, via a motor-drive, such that the imaging sensor 22, a digital camera for instance, moves circularly around the two feet/lower leg portions 26 of the client. Holder 20 with imaging sensor 22 typically stops in eight to twelve preselected, successive shooting positions 28. The position of the imaging sensor 22 and the shooting positions 28 are selected such that the images taken from each position take image cutouts overlapping each other and respectively containing the foot/leg portion 26 inclusive of at least some marks 10 of the support.

FIG. 2 shows a plan view of the support 12 with the feet 26 indicated schematically and the marks 10 which are photogrammetrically analysable on support 12. Imaging sensor 22 and the successively approached shooting positions 28 are represented as well. The camera is connected with a computer 30 for the evaluation of the images taken with the aid of methods of digital image processing and pattern recognition as well as photogrammetric methods. Ten shooting positions 28 are indicated; they are evenly distributed about the support 12. According to the respective body to be photographed, more or less or unevenly distributed shooting positions 28 are conceivable.

Since the photogrammetric evaluation of these overlapping shots calculates the position in space of the individual camera positions back from the marks of the support and the marks of the elastic cover, one need not know precisely the respective shooting positions. Thus, the accuracy of the mechanical camera guide and the individual shooting positions may be very low. The whole mechanism may be constructed to be simple, light and economical. It may perfectly be deformed under the influence of weight, of temperature fluctuations or other influences without the measuring accuracy suffering therefrom.

The invention claimed is:

1. A method for three-dimensional, digitized sensing of the spatial shape of bodies or body parts, comprising the steps of:
   covering the body, the body part or the body parts to be digitized with an elastic, tight-fitting cover which comprises high-contrast marks that are photogrammetrically analyzable,
   placing the body, the body part or the body parts onto a support which is also provided with marks that are photogrammetrically analyzable,
   mechanically moving at least one imaging sensor around the body, the body part or the body parts on a fixed path in space,
   taking image shots of the body, body part or body parts in successive shooting positions, whose image cutouts partially overlap each other, at least one said image is taken which covers both the body, the body part or the body parts and, simultaneously, a plurality of the marks of the support that are photogrammetrically analyzable, and
   evaluating in these image shots both the marks of the support and the marks on the tight-fitting cover by methods of photogrammetry and digital image processing and pattern recognition, such that the precise shooting positions in space of the imaging sensor and the precise space coordinates of the photographed body, the body part or the body parts are determined.

2. The method according to claim 1, wherein the at least one imaging sensor is moved mechanically on a circular path in space around the body, the body part or the body parts.

3. The method according to claim 1, wherein the at least one imaging sensor is moved mechanically on an elliptic path in space around the body, the body part or the body parts.

4. The method according to claim 1, wherein the at least one imaging sensor is moved by a motor-drive.

5. The method according to claim 1, wherein
   the at least one imaging sensor continuously takes or, respectively, take images during a continuous mechanical movement around the body, the body part or the body parts in the manner of a video camera, and
   automatically by evaluating the simultaneously photographed marks of the support which are photogrammetrically analyzable, using methods of pattern recognition, those individual images, which partially overlap each other, are determined that are sufficient for the photogrammetric evaluation.

6. The method according to claim 1, wherein the at least one image sensor may be adjusted in the vertical and/or azimuthal direction in addition to the mechanical movement around the body, the body part or the body parts.

7. The method according to claim 1, wherein, in the support which is provided with marks that are photogrammetrically analyzable and which is in contact with the body, the body part or the body parts, sensors further sense physical, physiological, medical or anatomical quantities.

8. The method according to claim 1, wherein the body, the body part or the body parts are biological bodies or body parts whose spatial shape is determined in order to choose or manufacture anatomically well-fitting clothes or orthopedic means to be true to size or to acquire anatomically or medically interesting data of the spatial shape.

9. The method according to claim 8, wherein the body parts are the two foot/lower leg portions of a person standing on a support provided with marks which are photogrammetrically analyzable and the sensed data of the spatial shape are used for the selection or for the custom manufacture of anatomically well-fitting footware.

10. The method according to claim 8, wherein the body part represents the lower body of a person standing on a support provided with marks which are photogrammetrically analyzable and the sensed data of the spatial shape are used for the selection or for the custom manufacture of anatomically well-fitting compression stockings, well-fitting tights or well-fitting trouser clothes.

11. The method according to claim 8, wherein, after photographing the body, the body part or the body parts covered with the elastic cover, the same undressed body, the body part or the body parts is/are photographed in approximately the same position.

12. The method according to claim 11, wherein the images of the undressed body, body part or the body parts are superimposed on the photogrammetrically established space coordinates in the form of a texture.

13. An arrangement for the three-dimensional, digitized sensing of the spatial shape of bodies or body parts, comprising:
   a support provided with high-contrast marks which are photogrammetrically analyzable serving as a floor area for the body, the body part or the body parts to be digitized, said body, body part or body parts being covered with an elastic, tight-fitting cover which also comprises marks which are photogrammetrically analyzable,
   at least one imaging sensor,
   at least one approximately vertical holder, to which the at least one imaging sensor is attached,
   a base on which the support rests and which carries along its periphery a mechanical guide along which the holder is guided,
   means for moving the holder together with the imaging sensor to successive shooting positions whose image cutouts overlap each other and simultaneously cover the body, the body part or the body parts to be digitized and several marks of the support, which are photogrammetrically analyzable,
   means for triggering image shots in the shooting positions, and
   a computer to which the images taken are transmitted and which comprises means for calculating by methods of image processing, pattern recognition and photogrammetry, the precise shooting positions in space of the imaging sensor and the spatial shape of the body, the body part or the body parts.

14. The arrangement according to claim 13, wherein the holder further carries at least one lighting means.

15. The arrangement according to claim 13, wherein the at least one image sensor on the holder may also be positioned in the vertical and/or azimuthal direction in addition to the peripheral positioning.

16. The arrangement according to claim 13, wherein the at least one holder may be tilted onto the plane of the base for transporting and for stowing away the arrangement.

17. The arrangement according to claim 13, wherein the means for moving said holder are motor-driven means.

18. The arrangement according to claim 17, wherein the base contains both the motor components needed for moving the at least one holder and the computer components required for acquiring the image data and for preprocessing and in situ evaluation.

19. The arrangement according to claim 13, wherein the support contains sensors for measuring physical, physiological, anatomical or medical quantities of a patient to be digitized.

20. A method for three-dimensional, digitized sensing of the spatial shape of bodies or body parts, comprising the steps of:
- covering the body, the body part or the body parts to be digitized with an elastic, tight-fitting cover which comprises high-contrast marks that are photogrammetrically analyzable,
- placing the body, the body part or the body parts onto a support which is also provided with marks that are photogrammetrically analyzable,
- mechanically moving at least one imaging sensor around the body, the body part or the body parts on a fixed path in space,
- taking continuously image shots of the body, body part or body parts with the imaging sensor(s) during a continuous mechanical movement around the body, the body part or the body parts in the manner of a video camera, the images covering both the body, the body part or the body parts and, simultaneously, a plurality of the marks of the support that are photogrammetrically analyzable,
- determining those individual images, which partially overlap each other, and that are sufficient for the photogrammetric evaluation, by evaluating automatically the simultaneously photographed marks of the support which are photogrammetrically analyzable, using methods of pattern recognition, and
- evaluating these image shots by methods of photogrammetry and digital image processing and pattern recognition, such that the precise space coordinates of the photographed body, the body part or the body parts are determined.

21. A method for three-dimensional, digitized sensing of the spatial shape of bodies or body parts, comprising the steps of:
- covering the body, the body part or the body parts to be digitized with an elastic, tight-fitting cover which comprises high-contrast marks that are photogrammetrically analyzable,
- placing the body, the body part or the body parts onto a support which is also provided with marks that are photogrammetrically analyzable,
- mechanically moving at least one imaging sensor around the body, the body part or the body parts on a fixed path in space,
- taking image shots of the body, body part or body parts in successive shooting positions, whose image cutouts partially overlap each other, at least one said image is taken which covers both the body, the body part or the body parts and, simultaneously, a plurality of the marks of the support that are photogrammetrically analyzable, and
- evaluating these image shots by methods of photogrammetry and digital image processing and pattern recognition, such that the precise space, coordinates of the photographed body, the body part or the body parts are determined, and
- sensing physical, physiological, medical or anatomical quantities by sensors contained in said support which is provided with marks that are photogrammetrically analyzable and which is in contact with the body, the body part or the body parts.

22. An arrangement for the three-dimensional, digitized sensing of the spatial shape of bodies or body parts, comprising:
- a support provided with high-contrast marks which are photogrammetrically analyzable serving as a floor area for the body, the body part or the body parts to be digitized, said body, body part or body parts being covered with an elastic, tight-fitting cover which also comprises marks which are photogrammetrically analyzable,
- at least one imaging sensor in the manner of a video camera,
- at least one approximately vertical holder, to which the at least one imaging sensor is attached,
- a base on which the support rests and which carries along its periphery a mechanical guide along which the holder is guided,
- means for moving the holder together with the imaging sensor in a continuous mechanical movement around the body, the body part or the body parts to be digitized, the at least one sensor continuously taking images during the movement, the images simultaneously covering the body and several marks of the support, which are photogrammetrically analyzable,
- means for automatically determining those individual images, which partially overlap each other, and that are sufficient for the photogrammetric evaluation, by evaluating the simultaneously photographed marks of the support which are photogrammetrically analyzable, using methods of pattern recognition, and
- a computer to which the images taken are transmitted and which calculates by methods of image processing, pattern recognition and photogrammetry, the spatial shape of the body, the body part or the body parts.

23. An arrangement for the three-dimensional, digitized sensing of the spatial shape of bodies or body parts, comprising:
- a support provided with high-contrast marks which are photogrammetrically analyzable serving as a floor area for the body, the body part or the body parts to be digitized, said body, body part or body parts being covered with an elastic, tight-fitting cover which also comprises marks which are photogrammetrically analyzable,
- at least one imaging sensor,
- at least one approximately vertical holder, to which the at least one imaging sensor is attached,
- a base on which the support rests and which carries along its periphery a mechanical guide along which the holder is guided,
- means for moving the holder together with the imaging sensor to successive shooting positions whose image cutouts overlap each other and simultaneously cover the body, the body part or the body parts to be digitized and several marks of the support, which are photogrammetrically analyzable, means for triggering image shots in the shooting positions, a computer to which the images taken are transmitted and which calculates by methods of image processing, pattern recognition and photogrammetry, the spatial shape of the body, the body part or the body parts, and sensors which are contained in the support for measuring physical, physiological, anatomical or medical quantities of a patient to be digitized.

* * * * *